United States Patent [19]

Cliffe

[11] Patent Number: 5,532,242
[45] Date of Patent: Jul. 2, 1996

[54] PIPERAZINE DERIVATIVES AS 5-HT RECEPTORS ANTAGONISTS

[75] Inventor: Ian A. Cliffe, Slough, England

[73] Assignee: John Wyeth & Brother, Limited, Maidenhead, England

[21] Appl. No.: 256,330

[22] PCT Filed: Dec. 24, 1992

[86] PCT No.: PCT/GB92/02399

§ 371 Date: Jul. 7, 1994

§ 102(e) Date: Jul. 7, 1994

[87] PCT Pub. No.: WO93/14076

PCT Pub. Date: Jul. 22, 1993

[30] Foreign Application Priority Data

Jan. 8, 1992 [GB] United Kingdom ............. 9200293

[51] Int. Cl.$^6$ .............. A61K 31/495; A61K 31/505; C07D 295/15; C07D 401/04
[52] U.S. Cl. .............. 514/255; 514/252; 544/238; 544/295; 544/357; 544/360; 544/393; 564/123
[58] Field of Search .................. 544/295, 393, 544/357, 360, 238; 514/252, 255

[56] References Cited

U.S. PATENT DOCUMENTS

| | | | |
|---|---|---|---|
| 3,037,982 | 6/1962 | Fancher et al. | 544/393 |
| 4,988,814 | 1/1991 | Abou-Gharbia et al. | 544/393 |
| 5,010,078 | 4/1991 | Abou-Gharbia et al. | 514/252 |
| 5,340,812 | 8/1994 | Cliffe | 514/255 |

FOREIGN PATENT DOCUMENTS

| | | |
|---|---|---|
| 015615 | 9/1980 | European Pat. Off. . |
| 048043 | 3/1982 | European Pat. Off. . |
| 048045 | 3/1982 | European Pat. Off. . |
| 190472 | 8/1986 | European Pat. Off. . |
| 343961 | 11/1989 | European Pat. Off. . |
| 496692 | 7/1992 | European Pat. Off. . |
| 2230781 | 10/1990 | United Kingdom . |

OTHER PUBLICATIONS

Cliffe et al, *Chemical Abstracts*, vol. 118, No. 169115 (1993) (Abstract for EP 512755, Nov. 11, 1992).

*Primary Examiner*—Emily Bernhardt
*Attorney, Agent, or Firm*—Arthur G. Seifert

[57] ABSTRACT

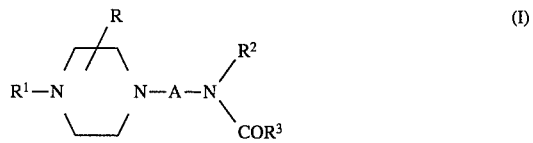

This invention concerns compounds of formula (I) where A is an alkylene chain of 2 to 5 carbon atoms optionally substituted by one or more lower alkyl groups, R represents hydrogen or one or two same or different lower alkyl groups, $R^1$ is a monocyclic aryl or heteroaryl radical, $R^2$ is a mono or bicyclic aryl radical and $R^3$ is cycloalkyl. The compounds of the invention are useful as antidepressant, antianxiety, or hypotensive agents; or for regulating the sleep/wake cycle, feeding behavior and/or sexual function; and for treating cognition disorders.

13 Claims, No Drawings

PIPERAZINE DERIVATIVES AS 5-HT RECEPTORS ANTAGONISTS

This application is a 371 of PCT/GB92/02399 filed Dec. 24, 1992.

This invention relates to piperazine derivatives, to processes for their preparation, to their use and to pharmaceutical compositions containing them. The novel compounds act on the central nervous system by binding to 5-HT receptors (as more fully explained below) and hence can be used as medicaments for treating humans and other mammals.

The novel compounds of the invention are those of the general formula

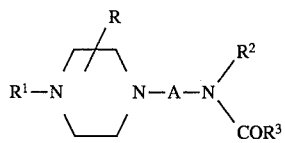

and the pharmaceutically acceptable acid addition salts thereof.

In formula (I)

A is an alkylene chain of 2 to 5 carbon atoms optionally substituted by one or more lower alkyl groups, R-represents hydrogen or one or two same or different lower alkyl groups, $R^1$ is a monocyclic aryl or heteroaryl radical, $R^2$ is a mono or bicyclic aryl radical and $R^3$ is cycloalkyl.

The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, tert-butyl, pentyl and isopentyl.

A cycloalkyl group can contain 3 to 12 carbon atoms. Preferably a cycloalkyl group is cyclopentyl, cyclohexyl or cycloheptyl, most preferably cyclohexyl. Cycloalkyl groups also include bicyclic, tricyclic and tetracyclic groups, e.g. adamantyl.

When used herein "a monocyclic aryl radical" means a phenyl radical which optionally may be substituted by one or more substituents and "a mono or bicyclic aryl radical" means an aromatic radical having 6 to 12 carbon atoms (eg phenyl or naphthyl) which optionally may be substituted by one or more substituents. Preferred substituents are lower alkyl, lower alkoxy (eg methoxy, ethoxy, propoxy, butoxy), halogen, halo(lower)alkyl (eg trifluoromethyl), nitro, nitrile, carbamoyl, (lower) alkoxycarbonyl, amino, (lower) alkylamino or di(lower)alkylamino substituents.

Preferably $R^1$ is a phenyl radical containing a substituent in the ortho position. A particularly preferred example of $R^1$ is o-(lower)alkoxyphenyl eg o-methoxyphenyl.

Preferably $R^2$ is an optionally substituted phenyl radical.

The term "monocyclic heteroaryl radical" refers to a monocyclic aromatic radical containing one or more hetero atoms (eg oxygen, nitrogen, sulphur) and which may be optionally substituted by one or more substituents. Examples of suitable substituents are given above in connection with "aryl" radicals. Preferably the monocyclic heteroaryl radical contains 5 to 7 ring atoms. Preferably the hetero ring contains a nitrogen hetero atom with or without one or more further hetero atoms. When $R^1$ is a heteroaryl radical it is preferably an optionally substituted pyrimidyl (particularly 2-pyrimidyl) radical.

Preferred compounds have the following substituents either independently or in combination:

(a) A is —(CH$_2$)$_2$—, —(CH$_2$)$_3$—or —(CH$_2$)$_4$—

(b) R is hydrogen (c) $R^1$ is o-methoxyphenyl (d) $R^2$ is phenyl (e) $R^3$ is cyclohexyl The compounds of the invention may be prepared by methods known in the art from known starting materials or starting materials that may be prepared by conventional methods.

One method of preparing the compounds of the invention comprises acylating an amine of formula

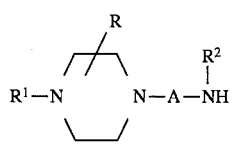

(where A, R, $R^1$ and $R^2$ have the meanings given above) with an acid of formula $$R^3COOH \qquad (III)$$

(where $R^3$ is as defined above) or with an acylating derivative thereof. Examples of acylating derivatives include the acid halides (eg acid chlorides) azides, anhydrides, imidazolides (eg obtained from carbonyldiimidazole), activated esters or O-acyl ureas obtained from a carbodiimide such as a dialkylcarbodiimide particularly cyclohexylcarbodiimide.

The starting amine of formula (II) may be prepared by a process such as that exemplified below:

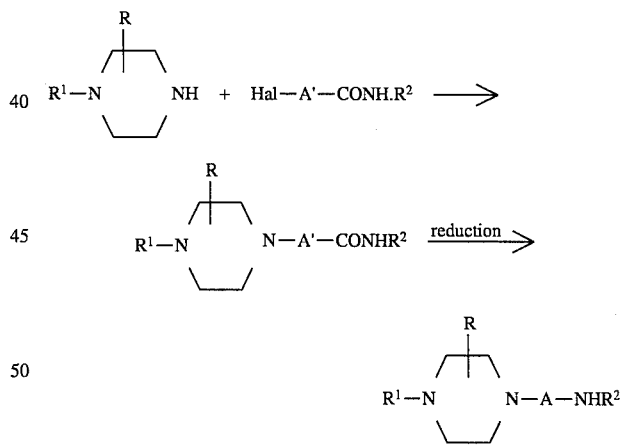

(where R, $R^{1,2}$, R and A are as defined above, Hal is halo, particularly chloro or bromo and A is an alkylene chain of 1 to 3 carbon atoms optionally substituted by one or more lower alkyl groups). The reduction may be carried out with, for example, a boron reducing agent eg borane-dimethyl sulphide.

A second method of preparing the compounds of the invention comprises alkylating an amide of formula (IV)

$$\underset{HN.COR^3}{R^2} \qquad (IV)$$

with an alkylating agent providing the group

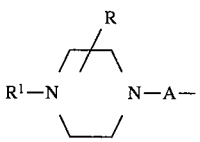

The alkylating agent may be, for example, a compound of formula

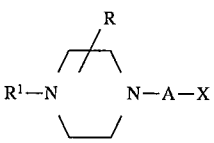

where A, R and $R^1$ are as defined above and X is a leaving group such as halogen or an alkyl—or aryl-sulphonyloxy group.

A third method of preparing the compounds of the invention comprises alkylating a compound of formula

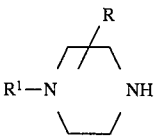

with a compound of formula $$X-A-NR^2.CO.R^3 \qquad (V)$$

(where A, R, $R^1$, $R^2$ and $R^3$ and X are as defined above). The starting compound of formula (V) may, for example, be prepared as exemplified below $$X-A-Br + NHR^2COR^3 \rightarrow \qquad (v)$$

Where $R^1$ is a group that is activated towards nucleophilic substitution the compounds of the invention may be prepared by a further method which comprises reacting the appropriate fluoro compound of formula $R^1F$ with a piperazine compound of formula

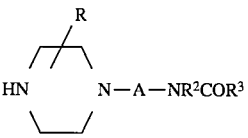

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention may contain one or more asymmetric carbon atoms, so that the compounds can exist in different steroisomeric forms. The compounds can be, for example, racemates or optically active forms. The optically active forms can be obtained by resolution of the racemates or by asymmetric synthesis. The compounds of the present invention possess pharmacological activity. In particular, they act on the central nervous system by binding to 5-HT receptors. In pharmacological testing it has been shown that the compounds particularly bind to receptors of the $5\text{-HT}_{1A}$ type. In general, the compounds selectively bind to receptors of the $5\text{-HT}_{1A}$ type to a much greater extent than they bind to other receptors such as $\alpha_1$ and $D_2$ receptors. Many exhibit activity as $5\text{-HT}_{1A}$ antagonists in pharmacological testing. The compounds of the invention can be used for the treatment of CNS disorders, such as anxiety in mammals, particularly humans. They may also be used as antidepressants, hypotensives, as agents for regulating the sleep/wake cycle, feeding behaviour and/or sexual function and for treating cognition disorders.

The compounds of the invention were tested for $5\text{-HT}_{1A}$ receptor binding activity in rat hippocampal membrane homogenate by the method of B S Alexander and M D Wood, J Pharm Pharmacol, 1988, 40, 888–891.

The compound of Example 2 which is a representative compound of the invention, had a $IC_{50}$ of 4 nM in this test procedure.

The compounds are tested for $5\text{-HT}_{1A}$ receptor antagonism activity in a test involving the antagonism of 5-carboxamidotryptamine in the guinea-pig ileum in vitro (based upon the procedure of Fozard et al, Br J Pharmac, 1985, 86, 601P). The results for compounds of the invention are given below. The compound of Example 2 had a $pA_2$ of 8.2.

The invention also provides a pharmaceutical composition comprising a compound or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (eg hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, eg from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, eg cellulose derivatives, preferably sodium carboxymethyl cellulose solution), alcohols (eg glycerol and glycols) and their derivatives, and oils (eg fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, eg as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention. Example 1 illustrates the preparation of an intermediate.

EXAMPLE 1

N-Phenyl cyclohexane carboxamide

Cyclohexanecarbonyl chloride (14.66 g, 0.1 mol) was added dropwise to a stirred solution of aniline hydrochloride (12.96 g 0.1 mol) and N, N-diisopropylethylamine (15.20 g, 0.2 mol) in dichloromethane (100 ml). The solution was stirred under an atmosphere of argon for 18 h, washed with 0.1 N-HCl (3×50 ml) and dilute sodium hydrogen carbonate solution (50 ml), dried (MgSO$_4$), and evaporated in vacuo to give the product (18.6 g) as white crystals.

EXAMPLE 2

N-(2-(4-(2-Methoxyphenyl)piperazin-1-yl)ethyl)-N-phenylcyclohexanecarboxamide A solution of the product of example 1 (2.03 g, 0.1 mol) in DMF (50 ml) was added dropwise to a suspension of potassium hydride, 35% dispersion in mineral oil (1.2 g, 0.011 mol) in DMF (20 ml). The suspension was stirred for 2 h, treated with 1-(2-chloroethyl)-4-(2methoxyphenyl)piperazine (2.53 g, 0.01 mol) stirred for 5 h at 80° C., cooled to room temperature, basified with dilute potassium carbonate solution, and evaporated in vacuo. The residue was dissolved in water (200 ml) and the solution extracted with ether (3×100 ml). The extracts were washed with water (100 ml), dried (MgSO$_4$), and evaporated in vacuo to give an oil which was purified by chromatography [silica; ethyl acetate-toluene (1:1) ]to give the product ( 0.41 g ) as a yellow oil. Addition of ethereal hydrogen chloride and evaporation gave the dihydrochloride salt of the product as a white solid, m.p. 118°–123° C. (Found: C, 62.6; H, 7.8; N, 8.2. C$_{26}$H$_{35}$N$_3$O$_2$. 2HCl.¼H$_2$O requires C, 62.6; H, 7.6; N, 8.4%).

I claim:
1. A compound of the formula

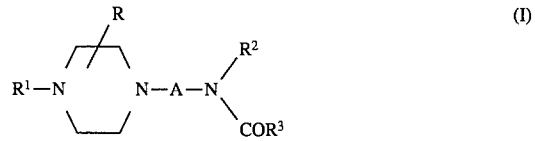

or a pharmaceutically acceptable acid addition salt thereof, wherein:

A is an alkylene chain of 2 to 5 carbon atoms optionally substituted by one or more lower alkyl groups;

R is hydrogen or one or two same or different lower alkyl groups;

R$^1$ is a phenyl or a 6-membered, monocyclic heteroaryl radical wherein the heteroatoms are selected from 1 or 2N atoms, which may be optionally substituted by 1 to 3 substituents independently selected from C$_1$–C$_6$alkyl, C$_1$–C$_6$alkoxy, halogen, haloC$_1$–C$_6$alkyl, nitro, nitrile, carbamoyl, C$_1$–C$_6$alkoxycarbonyl, amino C$_1$–C$_6$alkylamino or di-C$_1$–C$_6$alkylamino;

R$^2$ is phenyl or naphthyl, optionally substituted as for phenyl above; and

R$^3$ is monocycloalkyl 3 to 7 carbon atoms.

2. A compound as claimed in claim 1 in which A is —(CH$_2$)$_2$—, —(CH$_2$)$_3$— or —(CH$_2$)$_4$—.

3. A compound as claimed in claim 1 in which R$^1$ is o-methoxyphenyl.

4. A compound as claimed in claim 1 in which R$^2$ is phenyl.

5. A compound as claimed in claim 1 in which R$^3$ is cyclohexyl.

6. A compound as claimed in claim 1 which is N-(2-(4-(2-methoxyphenyl)piperazin-1-yl)ethyl)-N-phenylcyclohexanecarboxamide or a pharmaceutically acceptable acid addition salt thereof.

7. A pharmaceutical composition comprising a compound claimed in claim 1 in association with a pharmaceutically acceptable carrier.

8. A method of treating depression or anxiety in a mammal afflicted with the same, comprising administering to such mammal an amount effective to alleviate such depression or anxiety of a compound of the formula

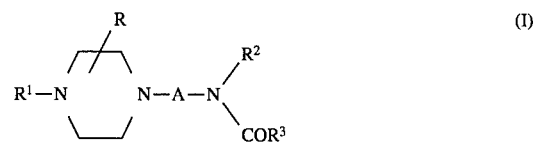

or a pharmaceutically acceptable acid addition salt thereof, wherein:

A is an alkylene chain of 2 to 5 carbon atoms optionally substituted by one or more lower alkyl groups;

R is hydrogen or one or two same or different lower alkyl groups;

R$^1$ is a phenyl or a 6-membered, monocyclic heteroaryl radical wherein the heteroatoms are selected from 1 or 2N atoms, which may be optionally substituted by 1 to 3 substituents independently selected from C$_1$–C$_6$alkyl, C$_1$–C$_6$alkoxy, halogen, halo C$_1$–C$_6$alkyl, nitro, nitrile, carbamoyl, C$_1$–C$_6$alkoxycarbonyl, amino, C$_1$–C$_6$alkylamino or di-C$_1$–C$_6$alkylamino;

$R^2$ is phenyl or naphthyl, optionally substituted as for phenyl above; and $R^3$ is monocycloalkyl of 3 to 7 carbon atoms.

9. A method of treatment according to claim 8 wherein A of a compound of formula I is —$(CH_2)_2$—, —$(CH_2)_3$— or —$(CH_2)_4$—.

10. A method of treatment according to claim 8 wherein $R^1$ of a compound of formula I is o-methoxyphenyl.

11. A method of treatment according to claim 8 wherein $R^2$ of a compound of formula I is phenyl.

12. A method of treatment according to claim 8 wherein $R^3$ of a compound of formula I is cyclohexyl.

13. A method of treatment according to claim 8 wherein the compound of formula I is n-(2-(4-(2-methoxyphenyl)piperazin-1-yl)ethyl)-N-phenylcyclohexanecarboxamide.

* * * * *